(12) United States Patent
Steinlechner et al.

(10) Patent No.: US 6,716,326 B2
(45) Date of Patent: Apr. 6, 2004

(54) CIRCUIT ARRANGEMENT FOR OPERATING AN EXHAUST-GAS PROBE

(75) Inventors: Siegbert Steinlechner, Leonberg (DE); Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 9 days.

(21) Appl. No.: 09/737,603

(22) Filed: Dec. 18, 2000

(65) Prior Publication Data

US 2003/0011373 A1 Jan. 16, 2003

(30) Foreign Application Priority Data

Dec. 16, 1999 (DE) ......................... 199 60 731

(51) Int. Cl.$^7$ ........................................... G01N 27/407
(52) U.S. Cl. ..................... 204/406; 204/425; 204/426; 204/427
(58) Field of Search ............... 204/421–429, 204/406

(56) References Cited

U.S. PATENT DOCUMENTS

| | | | |
|---|---|---|---|
| 5,810,997 A | * | 9/1998 | Okazaki et al. |
| 5,980,710 A | * | 11/1999 | Kurokawa et al. |
| 6,045,673 A | | 4/2000 | Kato et al. |
| 6,068,747 A | * | 5/2000 | Tojo et al. |
| 6,076,393 A | * | 6/2000 | Kato et al. |
| 6,228,252 B1 | * | 5/2001 | Miyata et al. |
| 6,319,377 B1 | | 11/2001 | Hasei et al. |
| 6,332,965 B1 | * | 12/2001 | Sugiyama et al. |

FOREIGN PATENT DOCUMENTS

| | | |
|---|---|---|
| DE | 198 52 247 | 6/1999 |
| EP | 0 831 322 | 3/1998 |
| GB | 2318186 | 4/1998 |
| GB | 2343761 | 5/2000 |
| WO | WO 98/13686 | 4/1998 |

OTHER PUBLICATIONS

"Electrochemical Methods" by A. J. Bard (1980), Fig. 13.4.6.

* cited by examiner

Primary Examiner—Kaj K. Olsen
(74) Attorney, Agent, or Firm—Walter Ottesen

(57) ABSTRACT

The invention is directed to a circuit arrangement for operating an exhaust-gas probe including a NOx double chamber sensor. The exhaust-gas probe includes: a heatable solid-state electrolyte body having first and second pump chambers and diffusion barriers for separating the chambers from each other and from the exhaust gas. A third chamber communicates with the atmosphere. An external pump electrode is exposed to the exhaust gas and a first oxygen pump electrode is disposed in the first pump chamber. A second oxygen pump electrode is disposed in at least one of the first and second pump chambers and a nitrogen oxide pump electrode is disposed in the second pump chamber. An air reference electrode is disposed in the third chamber. Only one pump voltage generating circuit unit is provided and a switching device switches the pump voltage generating circuit unit between respective ones of the pump electrodes. The pump voltage generating unit functions to generate, in a controlled manner, all of the voltages applied to the pump electrodes in dependence upon respective reference voltages.

10 Claims, 3 Drawing Sheets

_(page 1 of patent: column text)_

CIRCUIT ARRANGEMENT FOR OPERATING AN EXHAUST-GAS PROBE

FIELD OF THE INVENTION

The invention relates to a circuit arrangement for operating an exhaust-gas probe, especially an NOx probe.

BACKGROUND OF THE INVENTION

Exhaust-gas probes of this kind are used in motor vehicles for determining the excess-air factor (lambda) and the NOx values. These exhaust-gas probes are, in most cases, operated so that the potentials of the electrodes are fixedly set in a controlled manner and the pump currents are measured. This can, for example, take place via so-called potentiostats which are conventional in electrochemistry. A typical control circuit of such a potentiostat is disclosed, for example, in the publication of A. J. Bard entitled "Electrochemical Methods" (1980), FIGS. 13.4.6.

Control circuits of this kind include several operational amplifiers which all have different offsets. These different offsets of the operational amplifiers lead to errors in the measuring result of the exhaust-gas probes.

The offsets of the individual operational amplifiers add to a sum which is difficult to determine and which is also especially dependent upon temperature. To obtain a precise measuring result, a trimming of the individual operational amplifiers and their temperature characteristics is necessary.

SUMMARY OF THE INVENTION

It is an object of the invention to provide a circuit arrangement for operating an exhaust-gas probe which is so improved that the circuit arrangement makes possible the adjustment of the potentials having respective offsets which differ very little relative to each other.

Especially the above-mentioned matching or trimming of the operational amplifiers is to be avoided with the circuit arrangement of the invention.

The circuit arrangement of the invention is for operating an exhaust-gas probe including a NOx double chamber sensor. The exhaust-gas probe includes: a heatable solid-state electrolyte body having first and second pump chambers; diffusion barriers for separating the chambers from each other and from the exhaust gas; a third chamber communicating with the atmosphere; an external pump electrode exposed to the exhaust gas; a first oxygen pump electrode disposed in the first pump chamber; a second oxygen pump electrode disposed in at least one of the first and second pump chambers; a nitrogen oxide pump electrode disposed in the second pump chamber; an air reference electrode disposed in the third chamber; and, the circuit arrangement including: circuit means for applying pregivable voltages to the electrodes, respectively, and for generating, in a controlled manner, the following: a first oxygen pump current between the first oxygen pump electrode and the external pump electrode; a second oxygen pump current between the second oxygen pump electrode and the external pump electrode; and, a nitrogen oxide pump current between the nitrogen oxide pump electrode and the external pump electrode; and, the circuit means including: only one pump voltage generating circuit unit; switching means for switching the pump voltage generating circuit unit between respective ones of the pump electrodes; and, the pump voltage generating unit functioning to generate, in a controlled manner, all of the voltages applied to the pump electrodes in dependence upon respective reference voltages.

The pump voltage generating circuit unit can be switched over by a switching means between the individual pump electrodes and generates, in a controlled manner, all voltages applied to the pump electrodes in dependence upon the respective reference voltages. For this reason, all possibly occurring offsets of this pump voltage generating circuit unit are present to the same extent for all voltages applied to the pump electrodes and do not disturb the measuring result because only differences of the pump currents are measured in exhaust-gas sensors of this kind. The pump voltage generating circuit unit can be switched between the pump electrodes and therefore only one disturbing offset can occur. For this reason, no temperature compensation or trimming is needed in contrast to known circuits because of the circuit parts provided for each pump voltage. Furthermore, the generation of the pump voltage by only one single circuit unit is advantageous also with respect to the manufacture and assembly costs.

The pump voltage generating circuit unit advantageously has a single operational amplifier, which compares the reference voltages to the voltages applied to the pump electrodes and is switchable via the switching means and minimizes deviations of the voltages, which are applied to the pump electrodes, from the reference voltages. This operational amplifier is preferably a high precision balanced and temperature-compensated operational amplifier which has a minimal offset. A configuration of this kind of the pump voltage generating circuit unit is also especially cost effective. This is in addition to the technical advantages which are present in a small offset as well as an easy manipulation.

To minimize the deviation, the output of the operational amplifier is advantageously connected in each case via the switching means to three integrators assigned to the pump electrodes which integrate up the fault signals outputted by the operational amplifier. Three current measuring circuits are arranged downstream of the three integrators, respectively. The three current measuring circuits measure the pump currents flowing into the pump electrodes and output voltage values proportional thereto. In this way, three control loops are provided and possibly occurring offsets of the integrators and/or the current measuring circuits are insignificant for the measurement result to be obtained with the exhaust-gas probe. The only fault causing offset is generated by the pump voltage generating circuit unit in the form of an operational amplifier. This offset, however, occurs for all control loops in the same manner because the operational amplifier can be switched into the three control loops via the circuit means.

The circuit means is preferably configured in CMOS technology.

Operation is advantageously via a clock generator periodically with a frequency which preferably lies in the kilohertz range so that the operational amplifier is switched over in the kilohertz range into the three control circuits for generating the respective pump voltages at the individual electrodes.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
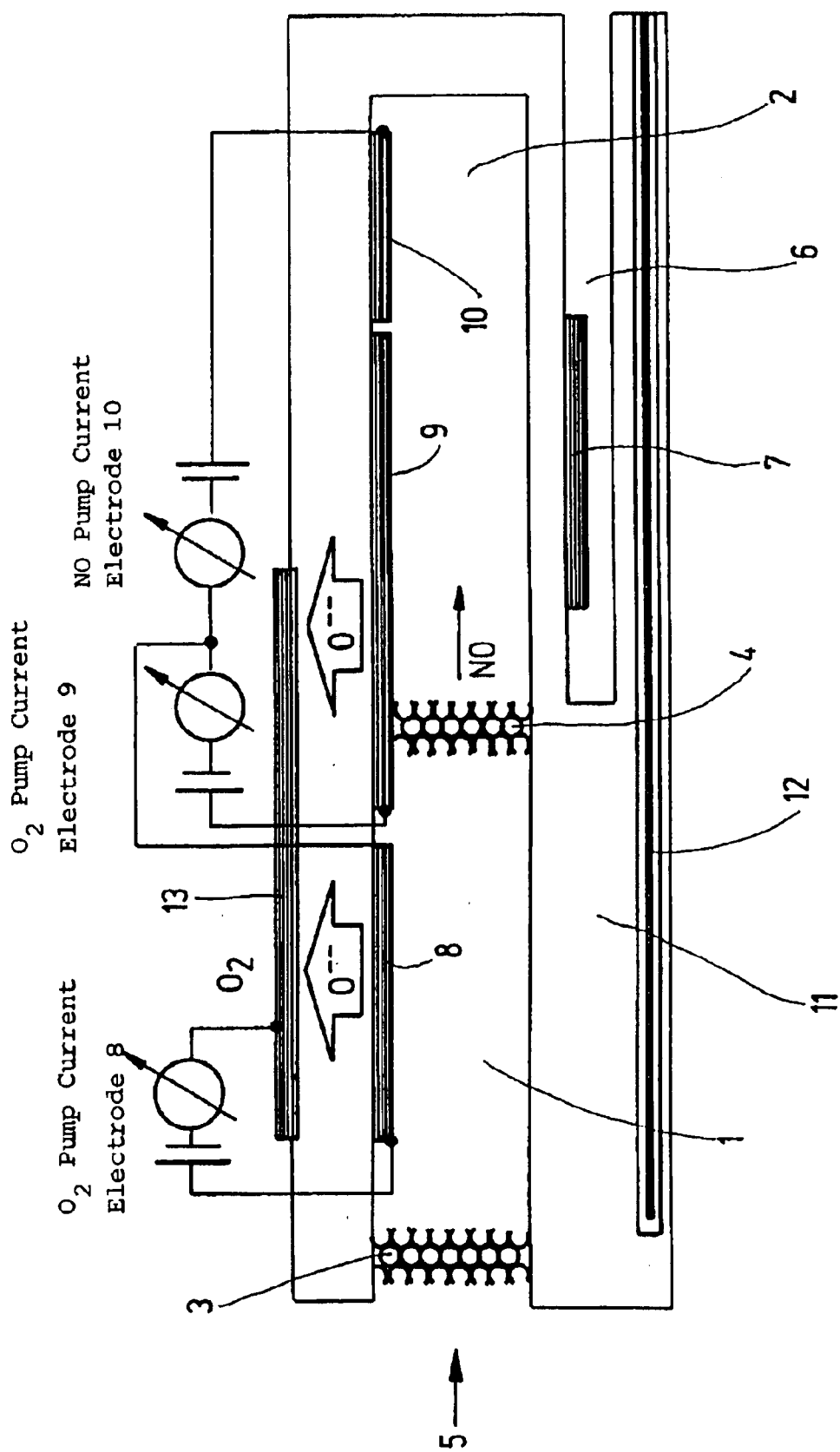
FIG. 1 is a section view of an NOx double chamber sensor used as an exhaust-gas probe.

An exhaust-gas probe in the form of an NOx double chamber sensor is shown in FIG. 1 and includes two pump chambers (1, 2) arranged in a solid electrolyte body 11. The pump chambers (1, 2) are connected to each other and to the exhaust gas 5 via diffusion barriers (3, 4). A third chamber 6 is connected to the ambient air and contains an air reference electrode 7.

In the first pump chamber 1, the oxygen is pumped away with the oxygen pump electrode 8 and, for this purpose, a second oxygen pump electrode 9 is used in the first and/or second pump chamber 1 or 2. An NOx pump electrode 10 is mounted behind or under the second oxygen pump electrode 9 and nitrous oxide is pumped away with the NOx pump electrode 10. The pump electrodes (8, 9, 10) are arranged in the solid state electrolyte body 11 which, for example, can comprise ion-conducting zirconium oxide.

An insulated heater having insulating layer 12 is arranged at the lower side of the sensor. The potentials of the pump electrodes (8, 9, 10) are adjusted to fixed values compared to the air reference electrode 7 via an electric control circuit (not shown in FIG. 1). A possible adjustment can, for example, be undertaken as follows:

oxygen pump electrode 8: reference point 0 V,
Air reference electrode 7: +300 mV,
Oxygen pump electrode 9: −100 mV,
NOx pump electrode 10: −105 mV.

For exhaust-gas probes of this configuration, it is purposeful to adjust the potentials via electrodes in a fixedly controlled manner and to measure the pump currents. This takes place via the circuit which will be explained in connection with FIG. 2.

Figure 2:
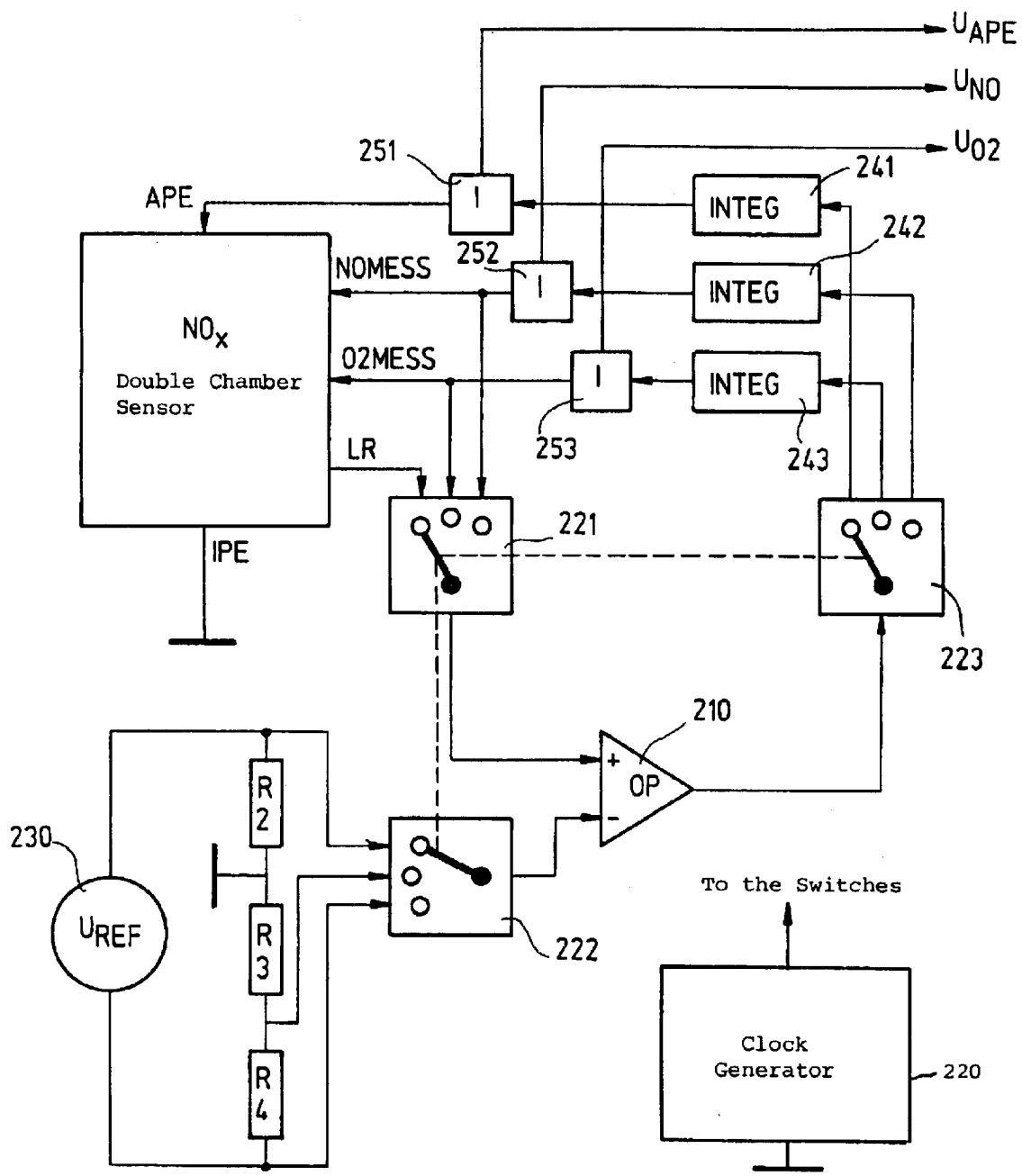
FIG. 2 shows schematically the circuit diagram of a circuit arrangement in accordance with an embodiment of the invention.

FIG. 2 shows the circuit block diagram of a circuit arrangement for operating the NOx double chamber sensor shown in FIG. 1. In FIG. 2, the following abbreviations are explained:

APE: external pump electrode 13,
NOMESS: NO pump electrode 10,
O2MESS: oxygen pump electrode 9,
LR: air reference electrode 7,
IPE: oxygen pump electrode 8.

Periodically, three voltage desired values are applied to the inverting input of an operational amplifier 210 via a circuit means 222, which can, for example, be configured in CMOS technology. The three voltage desired values are, for example, 300 mV, −100 mV and −105 mV. The voltage desired values are generated via a precise voltage source 230, for example, a band-gap reference having voltage dividers R2, R3, R4 as shown in FIG. 2. The operational amplifier 210 compares the voltage desired values to actual values at the electrodes LR, O2MESS and NOMESS. The selection of the actual value takes place synchronously with the selection of the desired value likewise via a switch means which switches the actual values at the electrodes to the non-inverting input of the operational amplifier 210. The amplified fault signal is applied to the output of the operational amplifier 210 and reaches respective ones of three integrators (241, 242, 243) via a further switching means 223 which operates synchronously. The three integrators (241, 242, 243) integrate the fault signal.

Figure 3:
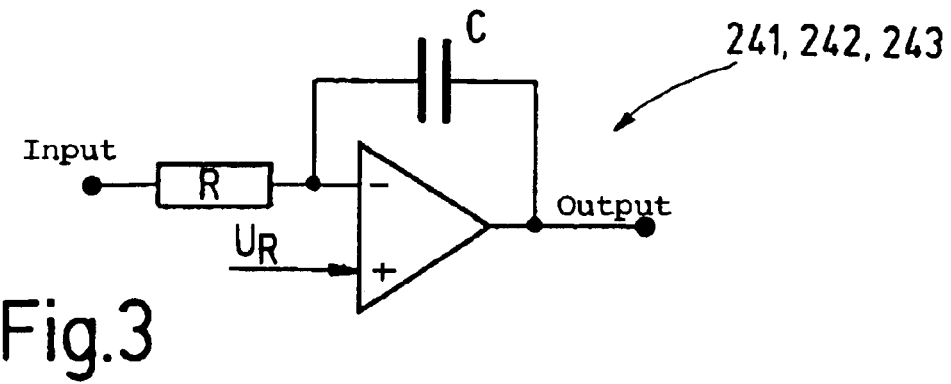
FIG. 3 is a schematic circuit diagram of an integrator of the circuit arrangement shown in FIG. 2; and, FIG. 4 shows a current measurement amplifier of the circuit arrangement shown in FIG. 2.
Figure 4:
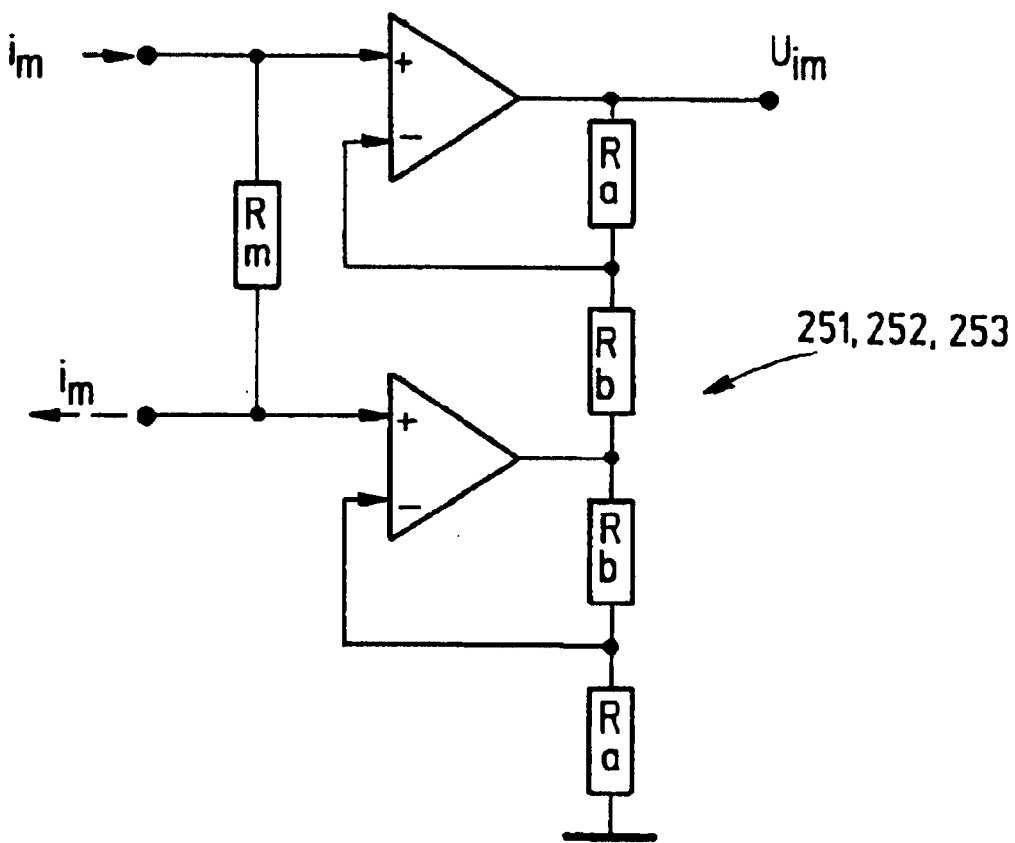

A circuit example of such an integrator is shown in FIG. 3 and is, for example, realized by an operational amplifier in an integrator circuit. The reference voltage UR is applied to the non-inverting input shown in FIG. 3 and is a fixed dc voltage which can be suitably selected. Current measuring circuits (251, 252, 253) are arranged at the outputs of the integrators (241, 242, 243). The current measuring circuits (251, 252, 253) measure the currents flowing into the sensor electrodes APE, NOMESS and O2MESS and supply the voltage values $U_{APE}$, $U_{NO}$ and $U_{O2}$ which are proportional thereto. A circuit for such a current measuring voltage is shown in FIG. 4 and can, in turn, be realized by an operational amplifier.

The circuit means (221, 222 and 223) are switchable via a clock generator 220 which effects the periodic switchover at a frequency which lies typically in the kilohertz range. The primary advantage of the above-described circuit arrangement is that the offsets of the operational amplifiers do not operate on the control of the voltages at the electrodes LR, O2MESS and NOMESS within the integrators (241, 242, 243) as well as the current measuring circuits (251, 252, 253). Only the offset voltage of the control amplifier in the form of the operational amplifier 210 operates on the voltages at these three electrodes in the same manner because the operational amplifier 210 generates voltages at all three electrodes via the clocked synchronous operation of switching means (221, 222, 223). And an offset, which operates on all electrodes in the same manner, is not critical with respect to the function of the exhaust-gas probe because only differences of the detected signals are of significance.

It is understood that the foregoing description is that of the preferred embodiments of the invention and that various changes and modifications may be made thereto without departing from the spirit and scope of the invention as defined in the appended claims.

What is claimed is:

1. A circuit arrangement for operating an exhaust-gas probe including a NOx double chamber sensor, said exhaust-gas probe including: a heatable solid-state electrolyte body having first and second pump chambers; diffusion barriers for separating said chambers from each other and from the exhaust gas; a third chamber communicating with the atmosphere; an external pump electrode exposed to the exhaust gas; a first oxygen pump electrode disposed in said first pump chamber; a second oxygen pump electrode disposed in at least one of said first and second pump chambers; a nitrogen oxide pump electrode disposed in said second pump chamber; an air reference electrode disposed in said third chamber; and, said circuit arrangement comprising;

circuit means for applying pregiven voltages to said electrodes, respectively, and for generating, in a controlled manner, the following: a first oxygen pump current between said first oxygen pump electrode and said external pump electrode; a second oxygen pump current from said second oxygen pump electrode via said first oxygen pump electrode to said external pump electrode; and, a nitrogen oxide pump current from said nitrogen oxide pump electrode via said first oxygen pump electrode to said external pump electrode; and, said circuit means including: only one pump voltage generating circuit unit; switching means for switching said pump voltage generating circuit unit between respective ones of said pump electrodes; and, said pump voltage generating unit functioning to generate, in a controlled manner, all of the voltages applied to said pump electrodes in dependence upon respective reference voltages.

2. The circuit arrangement of claim 1, said pump voltage generating circuit unit including an operational amplifier; said switching means being switchable to connect respective ones of said reference voltages and respective ones of said voltages applied to said pump electrodes to said operational amplifier which compares a corresponding one of said reference voltages to a corresponding one of said voltages applied to said pump electrodes; and, said pump voltage generating circuit unit further including means for minimizing deviations of each of said voltages applied to said pump electrodes from the corresponding one of said reference voltages.

3. The circuit arrangement of claim 2, said minimizing means including a plurality of integrators connected to corresponding ones of three of said pump electrodes; said switching means including ancillary switching means for connecting the output of said operational amplifier sequentially to said integrators which integrate corresponding ones of the fault signals outputted by said operational amplifier; a plurality of current measuring circuits connected downstream of corresponding ones of said integrators with said current measuring circuits measuring the pump currents flowing in respective ones of said pump electrodes and outputting voltage values proportional thereto.

4. The circuit arrangement of claim 1, said switching means being configured in CMOS technology.

5. The circuit arrangement of claim 1, further comprising a clock generator for periodically switching said switching means at a frequency in the kilohertz range.

6. A combination of an exhaust-gas probe and a circuit arrangement for operating the exhaust-gas probe, the combination including:

said exhaust-gas probe including: a heatable solid-state electrolyte body having first and second pump chambers; diffusion barriers for separating said chambers from each other and from the exhaust gas; a third chamber communicating with the atmosphere; an external pump electrode exposed to the exhaust gas; a first oxygen pump electrode disposed in said first pump chamber; a second oxygen pump electrode disposed in at least one of said first and second pump chambers; a nitrogen oxide pump electrode disposed in said second pump chamber; an air reference electrode disposed in said third chamber; and, said circuit arrangement including: circuit means for applying pregiven voltages to said electrodes, respectively, and for generating, in a controlled manner, the following: a first oxygen pump current between said first oxygen pump electrode and said external pump electrode; a second oxygen pump current from said second oxygen pump electrode via said first oxygen pump electrode to said external pump electrode; and, a nitrogen oxide pump current from said nitrogen oxide pump electrode and via said first oxygen pump electrode to said external pump electrode; and, said circuit means including: only one pump voltage generating circuit unit; switching means for switching said pump voltage generating circuit unit between respective ones of said pump electrodes; and, said pump voltage generating unit functioning to generate, in a controlled manner, all of the voltages applied to said pump electrodes in dependence upon respective reference voltages.

7. The combination of claim 6, said pump voltage generating circuit unit including an operational amplifier; said switching means being switchable to connect respective ones of said reference voltages and respective ones of said voltages applied to said pump electrodes to said operational amplifier which compares a corresponding one of said reference voltages to a corresponding one of said voltages applied to said pump electrodes; and, said pump voltage generating circuit unit further including means for minimizing deviations of each of said voltages applied to said pump electrodes from the corresponding one of said reference voltages.

8. The combination of claim 7, said minimizing means including a plurality of integrators connected to corresponding ones of three of said pump electrodes; said switching means including ancillary switching means for connecting the output of said operational amplifier sequentially to said integrators which integrate corresponding ones of the fault signals outputted by said operational amplifier; a plurality of current measuring circuits connected downstream of corresponding ones of said integrators with said current measuring circuits measuring the pump currents flowing in respective ones of said pump electrodes and outputting voltage values proportional thereto.

9. The combination of claim 6, said switching means being configured in CMOS technology.

10. The combination of claim 6, further comprising a clock generator for periodically switching said switching means at a frequency in the kilohertz range.

* * * * *